United States Patent
Kuri (10) Patent No.: US 9,408,541 B2
(45) Date of Patent: Aug. 9, 2016

(54) SYSTEM AND METHOD FOR DETERMINING ARTERIAL COMPLIANCE AND STIFFNESS

(71) Applicant: Yamil Kuri, Miami, FL (US)

(72) Inventor: Yamil Kuri, Miami, FL (US)

( * ) Notice: Subject to any disclaimer, the term of this patent is extended or adjusted under 35 U.S.C. 154(b) by 0 days.

(21) Appl. No.: 14/450,424

(22) Filed: Aug. 4, 2014

(65) Prior Publication Data

US 2016/0029901 A1    Feb. 4, 2016

(51) Int. Cl.

| | |
|---|---|
| *G06F 19/00* | (2011.01) |
| *A61B 5/00* | (2006.01) |
| *A61B 5/02* | (2006.01) |
| *A61B 5/0215* | (2006.01) |
| *A61B 5/022* | (2006.01) |
| *A61B 5/055* | (2006.01) |
| *A61B 8/06* | (2006.01) |

(52) U.S. Cl.
CPC ............ *A61B 5/02007* (2013.01); *A61B 5/022* (2013.01); *A61B 5/0215* (2013.01); *A61B 5/055* (2013.01); *A61B 5/7278* (2013.01); *A61B 8/06* (2013.01); *G06F 19/3431* (2013.01)

(58) Field of Classification Search
None
See application file for complete search history.

(56) References Cited

U.S. PATENT DOCUMENTS

| | | | | |
|---|---|---|---|---|
| 5,830,131 | A * | 11/1998 | Caro et al. | 600/300 |
| 5,836,884 | A * | 11/1998 | Chio | 600/485 |
| 6,511,436 | B1 | 1/2003 | Asmar | |
| 6,554,774 | B1 * | 4/2003 | Miele | 600/485 |
| 6,692,443 | B2 * | 2/2004 | Crutchfield et al. | 600/504 |
| 6,796,168 | B1 * | 9/2004 | Goldstein et al. | 73/54.01 |
| 7,048,691 | B2 * | 5/2006 | Miele et al. | 600/504 |
| 8,197,414 | B2 | 6/2012 | Quinn et al. | |
| 8,517,951 | B2 | 8/2013 | Fuji et al. | |
| 8,574,161 | B2 | 11/2013 | Banet et al. | |
| 8,657,755 | B2 * | 2/2014 | Parfenov et al. | 600/507 |
| 2003/0135124 | A1 * | 7/2003 | Russell | 600/500 |

(Continued)

OTHER PUBLICATIONS

Bude, Ronald O., and Jonathan M. Rubin. "Relationship between the Resistive Index and Vascular Compliance and Resistance." Radiology 211.2 (1999): 411-417.*

(Continued)

*Primary Examiner* — Gary Jackson
*Assistant Examiner* — Davin Sands
(74) *Attorney, Agent, or Firm* — Jacqueline Tadros, Esq.; Jacqueline Tadros, P.A.

(57) ABSTRACT

A system and method for calculating the arterial compliance, stiffness, and arterial flow and resistance indices for any artery in issue of a subject having a blood pressure monitoring device configured to calculate systolic and diastolic blood pressure readings for an artery of the subject, a blood flow velocity monitoring device configured to calculate the velocity of blood flowing within the artery of the subject at a peak point of a systolic phase of contraction of the subject's heart muscle, peak-systolic velocity, and the velocity of blood flowing within the artery of the subject at an end point of a diastolic phase of the subject's heart muscle, end-diastolic velocity, and a central processing unit comprising a computer readable program embodied within the central processing unit configured to calculate the arterial compliance, stiffness, and arterial flow and resistance indices as a function of the area of the artery under initial systolic and end diastolic pressure, the area of the artery generating arterial elastic recoil pressure for continuous flow during the systolic and diastolic phases, peak-systolic and end-diastolic arterial flow velocities, and systolic and diastolic blood pressure.

30 Claims, 4 Drawing Sheets

(56) References Cited

U.S. PATENT DOCUMENTS

| | | | |
|---|---|---|---|
| 2003/0216621 A1* | 11/2003 | Alpert et al. | 600/300 |
| 2004/0143319 A1 | 7/2004 | Schwartz et al. | |
| 2004/0243006 A1* | 12/2004 | Nakata et al. | 600/485 |
| 2007/0016083 A1* | 1/2007 | Hasegawa | 600/483 |
| 2007/0123779 A1* | 5/2007 | Hoctor et al. | 600/438 |
| 2009/0312653 A1 | 12/2009 | Sharrock et al. | |
| 2010/0292592 A1* | 11/2010 | Parfenov et al. | 600/507 |
| 2011/0009718 A1 | 1/2011 | Gavish | |
| 2011/0105918 A1 | 5/2011 | Fortin et al. | |
| 2011/0275944 A1 | 11/2011 | Qasem | |
| 2012/0283583 A1 | 11/2012 | Batkin et al. | |
| 2013/0184594 A1 | 7/2013 | Shelley et al. | |
| 2014/0213914 A1 | 7/2014 | Roteliuk | |

OTHER PUBLICATIONS

Pai, Ramdas G., and Pravin M. Shah. "Relationship between the pulse wave and the flow velocity wave and their propagation velocities in the arterial system: Implications for the assessment of regional physical properties of the arterial beds." International Journal of Angiology 8.2 (1999): 127-130.*

Artrial Stiffness and Hypertension, A Two Way Street? by Stanley S. Franklin, http://hyper.ahajournals.org/content/45/3/349.full, Feb. 14, 2005.

Systolic blood pressure pulse pressure and arterial stiffness (Safer, ME) http://www.ncbi.nlm.nih.gov/pubmed/11224702, Mar. 2001.

Assessment of arterial stiffness in clinical practice http://qjmed.oxfordjournals.org/content/95/2/67.long, Feb. 1, 2002.

Lowering of blood pressure and arterial stiffness by Peter Sleight http://www.thelancet.com/journals/lancet/article/PIIS0140-6736(05)62735-3/fulltext, Mar. 29, 1997.

Non invasive assessment of arterial stiffness using oscillometric blood pressure measure by Hidehiko Komine, Yoshiyuki Asai, Takashi Yokoi and Mutsuko Yoshizawa http://www.biomedical-engineering-online.com/content/11/1/6, Feb. 10, 2012.

Aortic stiffness current understanding and future directions, Apr. 2011 Joao L. Cavaicante, MC, Joao A.C. Lima, MD, MBA, Alban Redheul, MD PhD, Mouaz H. Al-Mallah, MD http://content.onlinejacc.org/article.aspx?articleID=1144323, Apr. 2011.

Methods for assessing arterial stiffness: technical considerations by Laurie A. Tomlinson http://www.aktn.org.au/publications/documents/PWVTomlinson.pdf, 2012.

Growth in utero, adult blood pressure and arterial compliance by CN Martyn, DJP Barker, S Jespersen, S Greenwald, C Osmond, C Berry British Heart Journal 1995; 73:116-121.

* cited by examiner

SP= Systolic Pressure (mm Hg)
DP= Diastolic Pressure (mm Hg)
PSV= Peak-Systolic Velocity (cm/sec or m/sec)
EDV= End-Diastolic Velocity (cm/sec or m/sec)

*FIG. 3*

| | | | | | | | | | | | | |
|---|---|---|---|---|---|---|---|---|---|---|---|---|
| SP | C | H | L | C | C | H | H | H | H | L | L | L | L |
| DP | C | C | C | H | L | H | H | H | L | H | L | L | L |
| ACI | C | L | H | H | L | H | C | L | L | H | L | C | L |
| ASI | C | H | L | L | H | L | C | H | H | L | H | C | H |
| SFI | C | H | L | L | H | H | H | H | H | L | L | L | H |
| SFRI | C | H | L | H | L | H | H | H | H | L | L | L | L |
| DFI | C | H | L | L | H | H | H | H | H | L | L | L | H |
| DFRI | C | L | H | H | L | H | H | H | L | H | L | L | L |

(Numerical values will indicate the magnitude of variance from baseline compliance)

*FIG. 4*

SYSTEM AND METHOD FOR DETERMINING ARTERIAL COMPLIANCE AND STIFFNESS

BACKGROUND OF THE INVENTION

1. Field of the Invention

This invention relates generally to a system, method and apparatus for determining arterial compliance and stiffness. In particular, the invention relates to a non-invasive quantitative system for calculating arterial elastic recoil pressure for vascular flow, arterial compliance, stiffness and arterial blood flow and resistance compliance. The method steps consist of modeling and combining arterial behavior from signature waveform flow velocities such as peak-systolic and end-diastolic arterial blood flow velocities and systemic blood pressure. The method determines the artery elastic recoil pressure for vascular blood flow as an Arterial Compliance Index ("ACI"), which correlates to blood pressure, artery distension, stiffness, arterial blood flow and resistance and is compared to a baseline index for a particular artery in issue.

2. Description of Related Art

The term elastic recoil pressure is used to describe the pressure exerted by the arterial walls when they recoil. Arterial elastic recoil pressure results from the distension and recoil of the artery necessary to regulate and maintain blood pressure and continued arterial blood flow.

The term arterial compliance is used to describe the flexibility of the arterial walls. Arterial compliance or distension results in the capacity of the artery to maintain blood flow by moving more volume with less pressure or distending more with less force applied.

The term arterial stiffness is used to describe the rigidity of the arterial walls. Arterial stiffness results in the incapacity of the artery to maintain blood flow by moving less volume with more pressure or distending less with more force applied.

The terms arterial blood flow and resistance are used to describe the flow and resistance to blood flow across the systemic arterial vasculature. Arterial blood flow resistance results in the incapacity of the systemic arterial vasculature to support blood flow by either increasing the arterial elastic recoil pressure thus reducing the pressure difference within the artery that pushes the blood or by increasing the force that opposes the blood flow through the vascular resistance.

Arterial compliance and stiffness assist in assessing soft and hard plaque formation on the artery walls, arterial inflammation, narrowing of arteries, arterial stenosis, local arterial function, arterial blood flow and resistance, systemic pressure and circulation in the peripheral arterial system, central pressure and circulation in the aorta. Also, Arterial compliance and stiffness can be associated with changes in heart rate and changes in the chemistry of body fluids naturally occurring or through the use of substances for medical or non-medical purposes. Thus, arterial compliance and stiffness are critical parameters for predicting and diagnosing both vascular and cardiovascular problems.

Current methods of measuring arterial stiffness are technically demanding, time consuming, costly, or limited in scope. It is therefore desirable to have an alternative comprehensive method which includes arterial blood flow velocities, elastic recoil pressure and systemic blood pressure, which can be used for any particular artery in issue and which can diagnose artery distension, stiffness, arterial blood flow and resistance in real time within the routine clinical setting.

Arterial compliance and stiffness depend on the functioning of muscle cells, elastin and collagen within the artery walls. These structural elements support the pressure of blood exerted on the artery wall when distended. Arteries distend and recoil in order to regulate and maintain blood pressure and continuous blood flow through the arterial system.

Presently known non-invasive methods and indices for measuring and quantifying arterial compliance and stiffness have several limitations in measurement and interpretation. For example, current methods and indices for measuring and quantifying arterial compliance and stiffness require expensive equipment, a high level of technical expertise and are often impractical or limited in scope within the routine clinical setting.

At this time, pulse wave velocity (PWV) analysis is the standard for diagnosing regional arterial stiffness. Pulse wave velocity is the speed at which a forward pressure wave is transmitted from the aorta or other major artery through the vascular tree. It is calculated by measuring the time it takes for the arterial waveform to pass between two points a measured distance apart.

The flow of blood through the arterial vasculature is influenced by the stiffness and elasticity of the vessel walls. With varying blood pressure and vascular resistance: The stiffer the arterial walls, the lower the elastic recoil pressure and the higher the blood flow. In elastic vessels, the higher the elasticity of the arterial walls, the higher the elastic recoil pressure and the lower the blood flow.

A current method to determine arterial blood flow resistance is based on what is called the Resistive Index ("RI") that relies only on blood flow velocities. The RI alone is inadequate to accurately assess arterial compliance, stiffness, flow and resistance.

Blood flow velocities can be determined from the arterial pulse waveforms along a vascular segment. Doppler ultrasound, Magnetic resonance imaging, positron emission tomography, Photoplethysmography, laser Doppler imaging, and laser speckle contrast imaging are used to measure blood flow velocities.

Stiff arteries result in higher systolic pressure, lower diastolic pressure and other blood pressure disorders because there is less elastic recoil to regulate the blood pressure. Thus, systolic and diastolic blood pressure, are both also important factors in predicting cardiovascular risk. Increased pulse pressure, increased heart rate at rest, and increased pulse wave velocity may be markers of underlying vascular disease or strong cardiovascular risks.

Pulse pressure is the difference between systolic and diastolic pressures, and depends on the cardiac output, large-artery stiffness and wave reflection. Thus the difference between systolic and diastolic pressure, that is the pulse pressure, will be expected to vary as the rigidity of the arterial walls. However, pulse pressure alone is inadequate to assess arterial stiffness accurately.

Thus, it is desirable to achieve an improved system, method and apparatus that combines the diagnostics of arterial flow velocities and systemic blood pressure readings for a particular artery in order to accurately determine the extent of artery distension and stiffness in real time and enable a comparison of a subject's artery distension and stiffness with a baseline index for the particular artery in issue.

SUMMARY OF THE INVENTION

The inventive method combines the velocities of blood flowing within an artery at points in time and systemic blood pressure to create a system and method that calculates an Arterial Compliance Index ("ACI"). The ACI or arterial elastic recoil pressure correlates to blood pressure, artery distension, stiffness, arterial blood flow and resistance and is compared to a Baseline Index ("BI") for the particular artery type under study in order to evaluate arterial compliance, stiffness, arterial blood flow and resistance. The BI is comprised of a mean of ACI indices obtained from screenings of normal functioning arteries among a group of subjects or established among segments of a subject's artery in issue as a baseline index. As used herein, the term arterial elastic recoil refers to the inherent resistance of a tissue to changes in shape, and the tendency of the tissue to revert to its original shape once deformed.

Specifically, the method steps consist of modeling and combining the arterial signature waveform blood flow velocities with systemic blood pressure using an arterial stiffness limit variable and an arterial recoil pressure variable in the system model, setting the area of the artery that is under initial systolic and end diastolic pressure to be equal, to determine the arterial elastic recoil pressure variable or Arterial Compliance Index "ACI".

The proposed system and method for determining local arterial compliance, stiffness, arterial blood flow and resistance compliance can be incorporated into Doppler ultrasound equipment or other devices for routine clinical screenings, thereby providing on-screen real time indices of arterial stiffness, and arterial blood flow and resistance. Blood pressure, systemic and regional arterial function, antegrade and retrograde flows can be evaluated with the proposed index from local arterial compliance and stiffness screening of different arteries.

The systemic blood pressure analysis of the present invention relies on systolic and diastolic blood pressure. Systolic blood pressure is the peak pressure in arteries near the end of the cardiac cycle when the heart is contracting. It is the top number of a typical blood pressure reading. Diastolic blood pressure is the pressure when the heart is near the end of the period of relaxation. It is the bottom number of a blood pressure reading.

The method of calculating the ACI allows for a determination of a specific baseline compliance index of a normal artery for each artery type. A diagnosis may therefore be made by considering the arterial compliance index and stiffness of arteries using peak-systolic and end-diastolic velocities; systemic and central arterial flow circulation as indicated by the systolic and diastolic blood pressure and other combined vascular parameters such as pulse pressure, resistive index, vascular resistance index and cardiac output index.

An aspect of the present invention is therefore to determine the peak-systolic velocity of the blood flowing through the artery at the end of the systolic phase and the end-diastolic velocity at the end of the diastolic phase of the blood flowing through the artery. The peak-systolic velocity and end-diastolic velocity may be determined using a device capable of calculating blood flow.

Another aspect of the present invention is to determine the area of the artery that is under initial systolic and end diastolic pressure, and the area of the artery that is generating arterial elastic recoil pressure for continuous flow during the systolic and diastolic phases. Yet another aspect of the present invention is to compare the area of the artery under initial systolic and end diastolic pressure with the area of the artery that is generating arterial elastic recoil pressure for continuous flow during the systolic and diastolic phases. It is noted that the term area is used throughout to denote the area index as defined herein.

It is noted that references made herein to the present invention or aspects of the invention thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

DETAILED DESCRIPTION OF THE DRAWINGS

The inventive method of the present invention is based on a combined analysis of blood pressure readings and the velocity of blood flow within an artery of a subject. The Arterial Compliance Index or ACI of the present invention therefore relies on blood pressure readings, blood flow velocities, the relationship between the area of the artery that is under initial systolic and end diastolic pressure, as well as the area of the artery that is generating arterial elastic recoil pressure for continuous flow during the systolic and diastolic phases, and a comparison of the area of the artery under initial systolic and end diastolic pressure with the area of the artery that is generating arterial elastic recoil pressure for continuous flow during the systolic and diastolic phases within a particular artery in order to determine arterial compliance, stiffness, and arterial flow and resistance compliance of the artery being studied. It is noted that the term area is used throughout to denote the area index as defined herein.

Figure 1:
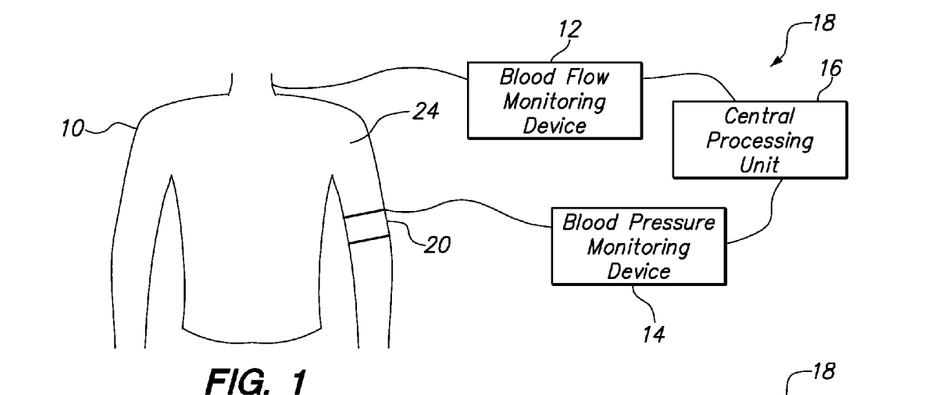
FIG. 1 is an illustration of a system of the present invention being used on a subject to determine the arterial compliance index, arterial stiffness, and the arterial flow and resistance indices.

Referring now to FIG. 1, the present invention is a system 18 for determining arterial compliance, stiffness, and arterial flow and resistance compliance in a subject 10. The system 18 includes a blood pressure monitoring device 14 for determining the systolic and diastolic blood pressure reading of the subject 10. The systolic pressure defined herein as SP refers to the pressure in the arteries when the heart beats, that is, when the heart contracts. The diastolic pressure, defined herein as DP measures the pressure in the arteries between heartbeats, that is, when the heart muscle is resting between beats and refilling with blood. Thus, in a typical blood pressure reading of 120/80 mmHg, the top number of 120 refers to the systolic blood pressure, that is SP and the lower number of 80 refers to the diastolic blood pressure, that is DP. The blood pressure monitoring device 14 includes a cuff 20 that is placed on a limb of the subject 10. In a preferred embodiment, the cuff 20 is placed on an arm 24 of the subject 10. In an alternative embodiment, the cuff 20 may be placed on a lower limb (not shown here) or another body part that will allow a blood pressure reading to be taken.

The system 18 further includes a blood flow monitoring device 12 for measuring the peak-systolic velocity or PSV and end-diastolic velocity or EDV of blood flow within the subject's 10 artery. The PSV refers to the peak velocity of the blood flow during systole, when the heart contracts. The EDV refers to the blood velocity at the end of the diastolic phase when the heart muscle is at rest and the heart refills with blood. It is noted that the PSV and EDV are measured for a particular artery under study, for example, a carotid or renal artery.

The system 18 further includes a central processing unit comprising a non-transitory computer-readable media embodied within the central processing unit 16 configured to calculate the arterial compliance index or ACI, stiffness, and arterial flow and resistance indices of the subject 10.

Figure 1A:
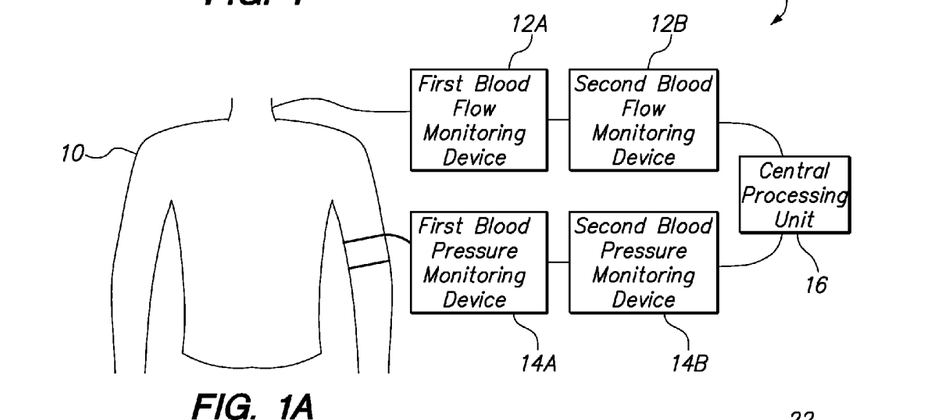
FIG. 1A is an alternative embodiment of a system of the present invention being used on a subject to determine the arterial compliance index, arterial stiffness, and the arterial flow and resistance indices.

Referring now to FIG. 1A there is shown an alternative embodiment of the system 18 of the present invention. In this alternative embodiment, the system includes a first blood flow monitoring device 12A configured to calculate a first measure of velocity of blood flowing within the artery of the subject at a peak point of a systolic phase of contraction of the subject's 10 heart muscle, PSV and a second blood flow monitoring device 12B configured to calculate a second measure of velocity of blood flowing within the artery of the subject 10 at an end point of a diastolic phase of the subject's heart muscle, EDV.

The system 18 further includes a first blood pressure monitoring device 14A configured to calculate a systolic blood pressure, SP, reading for an artery of the subject 10, and a second blood pressure monitoring device 14B configured to calculate the diastolic blood pressure reading, DP. The system 18 further includes a central processing unit comprising a non-transitory computer-readable media embodied within the central processing unit 16 configured to calculate the arterial compliance index or ACI, stiffness, arterial flow and resistance indices of the subject 10, as a function of the area of the artery under initial systolic pressure and end diastolic pressure and the area of the artery generating arterial elastic recoil pressure for continuous flow during the systolic and diastolic phases.

In an invasive embodiment, the first blood pressure monitoring device, 14A and the second blood pressure monitoring device 14B, each comprise a catheter device for taking blood pressure readings within an artery of the subject 10. It should be appreciated that the blood pressure monitoring device 14 shown in FIGS. 1 and 1B may also comprise a catheter device for taking a blood pressure reading within an artery of the subject 10.

Figure 1B:
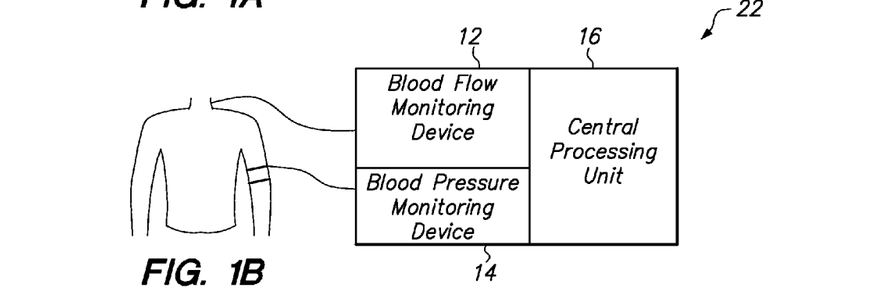
FIG. 1B is another embodiment of a system of the present invention being used on a subject to determine the arterial compliance index, arterial stiffness, and the arterial flow and resistance indices.

Referring now to FIG. 1B, there is shown another embodiment of the present invention, wherein the blood flow monitoring device 12, the blood pressure monitoring device 14 and the central processing unit 16 all comprise a single unit 22.

Figure 2:
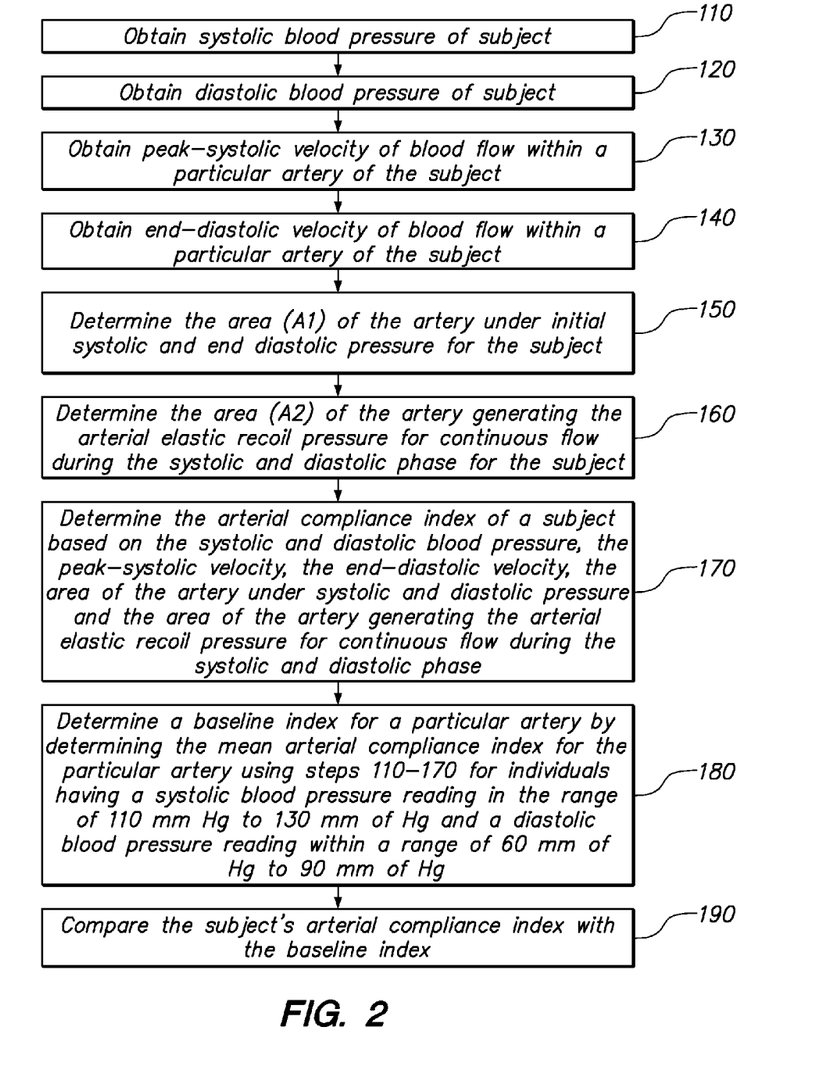
FIG. 2 is a flow chart outlining the method of the present invention for determining the arterial compliance index for the particular artery in issue of a subject.

Referring now to FIG. 2, there is shown a flow chart that illustrates a method of the present invention. A first step 110, of the method of the present invention is to obtain a systolic blood pressure reading SP for the subject 10. A second step 120, of the method of the present invention is to obtain a diastolic blood pressure reading DP for the subject 10. A third step, 130, of the method of the present invention is to obtain a peak-systolic velocity reading of blood flow, PSV, within a particular artery of the subject 10. A fourth step, 140, of the method of the present invention is to obtain an end-diastolic velocity reading of blood flow, EDV, within a particular artery of the subject 10. The fifth step, 150, of the method of the present invention is to calculate the area of the artery that is under initial systolic and end diastolic pressure A1=(PSV−EDV)/(SP−DP) or inverse vascular resistance index, VRI=1/A1. The sixth step, 160, of the method of the present invention is to calculate the area of the artery that is generating the arterial elastic recoil pressure for continuous flow during the systolic and diastolic phase A2 for the subject 10.

In particular, the area of the artery that is generating the arterial elastic recoil pressure for continuous flow or A2 is determined as follows:

$$A2 = \frac{(-XZ/Y) + \sqrt{(XZ/Y)^2 + 4(A1)^2}}{2}$$

Where: $A1 = (PSV - EDV)/(SP - DP)$ $X = (A1/A2)_{SL} - 1$ $(A1/A2)_{SL} = ((SP + dSP)/SP)$ ($dSP$ = any small change in $SP$, i.e. 0.1, 0.01, 0.0001)

and $Y = SP(A1/A2)_{SL}$ $Z = SP(A1) - PSV$ $SL$ – Stiffness limit of the artery The seventh step, 170, of the method of the present invention is to determine the arterial compliance index of the subject 10 based on the systolic blood pressure, SP, the diastolic blood pressure, DP, the peak-systolic velocity, PSV, the end-diastolic velocity, EDV, the area of the artery under initial systolic and end diastolic pressure A1 and the area of the artery generating the arterial elastic recoil pressure for continuous flow during the systolic and diastolic phase A2. In particular, the arterial compliance index or ACI is determined as follows:

ACI=(SP($A1$)−PSV)/$A2$ or ACI=(DP($A1$)−EDV)/$A2$

Alternatively, the arterial compliance index of the subject 10 can be determined based on the systolic blood pressure, SP, the diastolic blood pressure, DP, the peak-systolic velocity, PSV, the end-diastolic velocity, EDV, the area of the artery under initial systolic and end diastolic pressure A1 and the area of the artery generating the arterial elastic recoil pressure for continuous flow during the systolic and diastolic phase A2. A1 is the area under initial systolic and end diastolic pressure (same area for both), arterial equilibrium area index or inverse of vascular resistance index (vascular resistance index, VRI=1/A1) and A2 is the area generating the arterial elastic recoil pressure for continuous flow during the systolic and diastolic phase. In particular, the arterial compliance index or ACI is alternatively determined as follows:

$$ACI = 1 + \frac{\sqrt{1+4wx}}{2w}$$

Where: $w = \dfrac{x(A1)^2}{(SP(A1) - PSV)^2}$ and $x = \dfrac{SP(A1/A2)_{SL}}{(A1/A2)_{SL}^2 - 1}$ $A1 = (PSV - EDV)/(SP - DP)$ -continued $$A2 = \frac{SP(A_1) - PSV}{ACI}$$

SP = Systolic Blood Pressure

DP = Diastolic Blood Pressure

PSV = Peak-Systolic Velocity of Blood Flow

EDV = End-Diastolic Velocity of Blood Flow

A1 = Equilibrium area index of the artery under initial systolic and end diastolic pressure = inverse of vascular resistance index = 1/VRI A2 = Area index of the artery generating arterial elastic recoil pressure for continuous flow during the systolic and diastolic phases.

SL = Stiffness limit of the artery

The SL is reached when there is no elastic recoil pressure in the artery, the artery reaches the systolic pressure without stretching, at which point A1 is substantially equal to A2. The derivation of the ACI index described herein is further simplified to:

ACI=(DP(PSV)−SP(EDV))/(PSV−EDV), or

ACI=(SP(EDV)−DP(PSV))/(EDV−PSV)

The ACI index is further expressed as a function of systolic and diastolic blood pressure in combination with at least one of the vascular parameters: pulse pressure, systolic resistive index, diastolic resistive index, vascular resistance index, systolic vascular resistance pressure, diastolic vascular resistance pressure and cardiac output index as:

ACI=SP−[PSV(SP−DP)/(PSV−EDV)], or

ACI=DP−[EDV(SP−DP)/(PSV−EDV)]

Where,

Pulse Pressure (PP)=(SP−DP)

Systolic Resistive Index (SRI)=(PSV−EDV)/PSV

Diastolic Resistive Index (DRI)=(PSV−EDV)/EDV

Vascular Resistance Index (VRI)=(SP−DP)/(PSV−EDV)

Systolic Vascular Resistance Pressure (SVRP)=[PSV(SP−DP)/(PSV−EDV)]

Diastolic Vascular Resistance Pressure (DVRP)=[EDV(SP−DP)/(PSV−EDV)]

Cardiac Output Index (COI)=(PSV−EDV)

Thus,

ACI=(DP(PSV)−SP(EDV))/COI, or

ACI=(DP/SRI)−(SP/DRI), or

ACI=SP−(PP/SRI)=SP−PSV(VRI)=SP−PSV(PP/COI)=SP−SVRP, or

ACI=DP−(PP/DRI)=DP−EDV(VRI)=DP−EDV(PP/COI)=DP−DVRP

The arterial stiffness index (ASI) is shown as the ACI of the artery under study divided by the ACI of the baseline artery, such that if the arterial stiffness index is equal to one, there is compliance, if the arterial stiffness index is more than 1, the artery stiffness is below baseline (more elastic) with a lower blood flow. If the arterial stiffness index is less than one, the artery stiffness is above baseline (stiffer) with a higher blood flow.

The eighth step, 180, of the method of the present invention is to determine a baseline index for a particular artery under study, that is the artery of the subject 10 that is under study, for example, the carotid or the left or right renal artery. The baseline index is determined by repeated steps 110 through 170 for different segments of the subject's artery or for a group of individuals having normal functioning arteries with a systolic blood pressure reading in the range of 110 mmHg to 130 mmHg and a diastolic blood pressure reading within a range of 60 mmHg to 90 mmHg and taking the mean reading. In a preferred embodiment, only individuals with systolic blood pressure readings proximate to 120 mmHg and diastolic blood pressure readings proximate to 80 mmHg are used to determine the baseline index. This threshold can be optimized by evaluating the baseline indices of the selected individuals and by further considering the heart rate of the selected individuals. Thus, the baseline index relating to a particular artery in issue may be derived from a mean of arterial compliance indices obtained from a segment of a population.

The ninth step, 190, of the method of the present invention is to compare the subject's arterial compliance index with the baseline index for the particular artery under study. Where the arterial compliance index ACI of the subject 10 falls below the baseline index, there is shown to be arterial stiffness. If the arterial stiffness index, ASI=ACI (artery in issue)/ACI (baseline) is equal to 1 then the artery in issue is compliant; if greater than 1 then the artery in issue is less stiff than baseline (more elastic); if lower than 1 then the artery in issue is stiffer than baseline. The lower or higher the stiffness index is from 1, the stiffer or less stiff the artery is from baseline respectively. It is noted that the group of subjects may be further categorized by age group.

Figure 3:
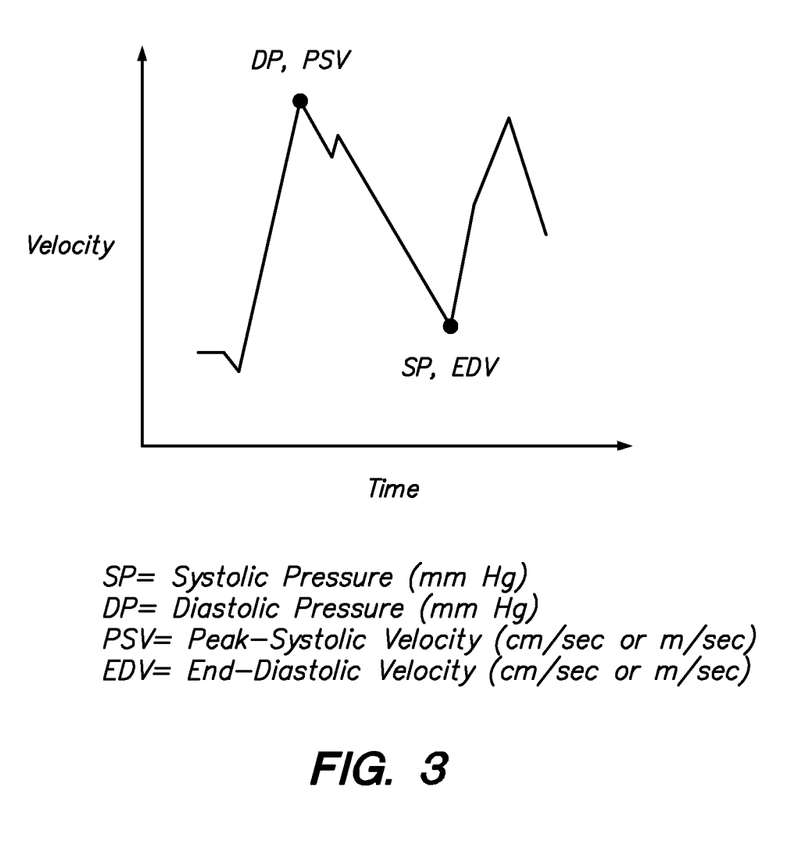
FIG. 3 is a graph that plots the velocity of blood flow as a function of time. The graph shows the peak-systolic velocity, PSV, the systolic pressure SP, the end-diastolic velocity EDV and the diastolic pressure DP, in relation to time.

Referring now to FIG. 3, there is shown a graph that plots the velocity of blood flow as a function of time. The graph shows the peak-systolic velocity, PSV, the systolic pressure SP, the end-diastolic velocity EDV and the diastolic pressure DP, in relation to time.

Figure 4:
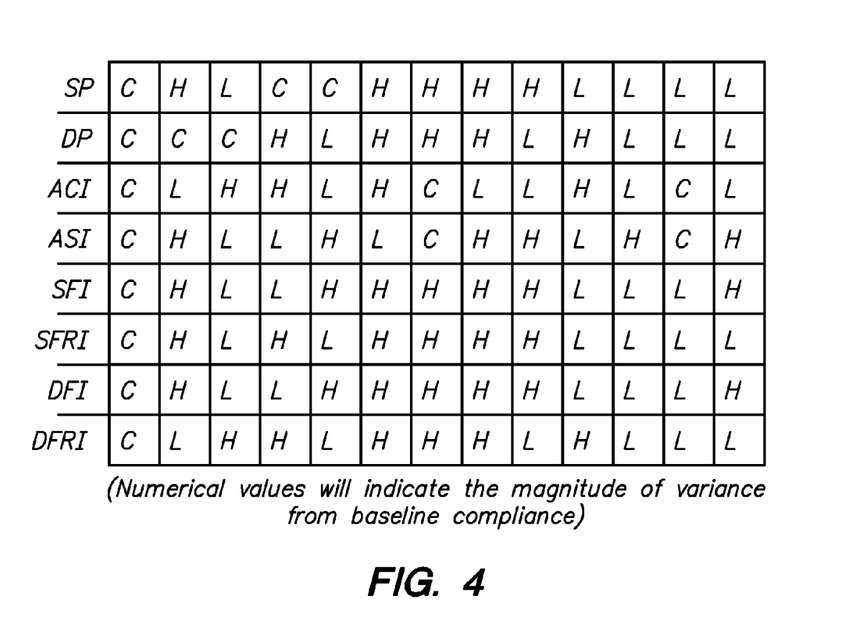
FIG. 4 is a diagram illustrating systemic blood pressure combinations as they relate to the arterial compliance index (ACI) or arterial elastic recoil pressure for vascular flow, arterial compliance, stiffness, and systolic and diastolic arterial blood flow and resistance.

Referring now to FIG. 4 there is shown a diagram illustrating a few systemic blood pressure combinations which can be evaluated and how they relate to the arterial compliance index (ACI) or arterial elastic recoil pressure for vascular flow, arterial compliance, stiffness, and systolic and diastolic arterial blood flow and resistance; where, SP is the Systolic blood pressure; DP is the Diastolic blood pressure; C is the Compliant or equal to baseline index; H is the Higher than baseline index; L is the Lower than baseline index. Numerical values inserted in place of the various measurements, namely, SP, DP, ACI, ASI, SFI, SFRI, DFI, DFRI, VRI, C, H and L, will indicate the magnitude of variance from baseline compliance.

| CASE | 1 | 2 | 3 | 4 | 5 | 6 | 7 | 8 |
|------|---|---|---|---|---|---|---|---|
| SP   | H | L | C | C | H | H | L | L |
| DP   | C | C | H | L | H | L | H | L |

Systolic Flow Index $$SFI = 1 - \sqrt{(ACI/SP)}$$

Systolic Flow Resistance Index $$SFRI = (SP-ACI)/(1-\sqrt{(ACI/SP)})$$

Diastolic Flow Index $$DFI = 1 - \sqrt{(ACI/DP)}$$

Diastolic Flow Resistance Index $$DFRI = (DP-ACI)/(1-\sqrt{(ACI/DP)})$$

Vascular Resistance Index $$VRI = (SP-ACI)/PSV = (DP-ACI)/EDV = (SP-DP)/(PSV-EDV)$$

EXAMPLE 1

Renal Artery Evaluation

| BASE LINE SUBJECT DATA | STUDY SUBJECT DATA |
| --- | --- |
| SP = 120 mm Hg | SP = 162 mm Hg |
| DP = 80 mm Hg | DP = 103 mm Hg |
| PSV = 56.54 cm/sec | PSV = 68.1 cm/sec |
| EDV = 20.76 cm/sec | EDV = 25 cm/sec |
| CALCULATED INDICES | CALCULATED INDICES |
| ACI = 56.8 mmHg | ACI = 68.8 mmHg |
| SFI = 0.312 | SFI = 0.348 |
| SFRI = 202.559 | SFRI = 267.555 |
| DFI = 0.157 | DFI = 0.183 |
| DFRI = 147.409 | DFRI = 187.167 |
| VRI = 1.118 | VRI = 1.369 |

Comparison of calculated indices:
1. ACI of study subject is higher than the baseline index indicating that the subject artery is non-compliant, the arterial stiffness index (ASI)=ACI (study)/ACI (baseline)=68.8/56.8=1.211>1, the artery in issue is less stiff than baseline (more elastic).
2. SFI of study subject is higher than the baseline index indicating that systolic blood flow through the artery of the study subject is higher than baseline, SFI (study)/SFI (baseline)=0.348/0.312=1.117

3. SFRI of study subject is higher than the baseline index indicating that systolic blood flow resistance through the artery of the study subject is higher than baseline, SFRI (study)/SFRI (baseline)=267.555/202.559=1.321

4. DFI of study subject is higher than the baseline index indicating that diastolic blood flow through the artery of the study subject is higher than baseline, DFI (study)/DFI (baseline)=0.183/0.157=1.162

5. DFRI of study subject is higher than the baseline index indicating that diastolic blood flow resistance through the artery of the study subject is higher than baseline, DFRI (study)/DFRI (baseline)=187.167/147.409=1.27

6. The VRI of study subject is higher than the baseline index indicating that vascular resistance of the study subject is higher than baseline, VRI (study)/VRI (baseline)=1.369/1.118=1.224

EXAMPLE 2

Carotid Artery Evaluation

| BASE LINE SUBJECT DATA | STUDY SUBJECT DATA |
| --- | --- |
| SP = 120 mm Hg | SP = 161 mm Hg |
| DP = 80 mm Hg | DP = 91 mm Hg |
| PSV = 83.2 cm/sec | PSV = 131 cm/sec |
| EDV = 14.9 cm/sec | EDV = 61 cm/sec |
| CALCULATED INDICES | CALCULATED INDICES |
| ACI = 71.3 mmHg | ACI = 30 mmHg |
| SFI = 0.229 | SFI = 0.568 |
| SFRI = 212.499 | SFRI = 230.498 |
| DFI = 0.056 | DFI = 0.426 |
| DFRI = 155.525 | DFRI = 143.249 |
| VRI = 0.586 | VRI = 1 |

Comparison of calculated indices:
1. ACI of study subject is lower than the baseline index indicating that the subject artery is non-compliant, the arterial stiffness index (ASI)=ACI (study)/ACI (baseline)=30/71.3=0.421<1, the artery in issue is stiffer than baseline.
2. SFI of study subject is higher than the baseline index indicating that systolic blood flow through the artery of the study subject is higher than baseline, SFI (study)/SFI (baseline)=0.568/0.229=2.48

3. SFRI of study subject is higher than the baseline index indicating that systolic blood flow resistance through the artery of the study subject is higher than baseline, SFRI (study)/SFRI (baseline)=230.498/212.499=1.085

4. DFI of study subject is higher than the baseline index indicating that diastolic blood flow through the artery of the study subject is higher than baseline, DFI (study)/DFI (baseline)=0.426/0.056=7.612

5. DFRI of study subject is lower than the baseline index indicating that diastolic blood flow resistance through the artery of the study subject is lower than baseline, DFRI (study)/DFRI (baseline)=143.249/155.525=0.921

6. The VRI of study subject is higher than the baseline index indicating that vascular resistance of the study subject is higher than baseline, VRI (study)/VRI (baseline)=1/0.586=1.708

GLOSSARY

SP=Systolic blood pressure (mmHg)
DP=Diastolic blood pressure (mmHg)
PP=Pulse pressure (mmHg)
PSV=Peak-systolic velocity (cm/sec or m/sec)
EDV=End-diastolic velocity (cm/sec or m/sec)
ACI=Arterial Compliance Index or arterial elastic recoil pressure (mmHg)

ASI=Arterial stiffness index
SFI=Arterial systolic flow index
SFRI=Arterial systolic flow resistance index
DFI=Arterial diastolic flow index
DFRI=Arterial diastolic flow resistance index
VRI=Vascular Resistance Index
SVRP=Systolic Vascular Resistance Pressure (mmHg)
DVRP=Diastolic Vascular Resistance Pressure (mmHg)
SRI=Systolic Resistive Index
DRI=Diastolic Resistive Index
COI=Cardiac Output Index
BI=Arterial baseline Index for ACI, ASI, SFI, SFRI, DFI, DFRI, VRI, SVRP, DVRP, SRI, DRI and COI
A1=Arterial equilibrium area index=inverse of vascular resistance index=1/VRI
A2=Arterial elastic recoil area index Thus, the relationship between arterial equilibrium area index and elastic recoil area index is A1/A2. Further, the higher the value of the VRI the higher the vascular resistance. High values of A1 (low VRI) with or without stiffness represent arterial stenosis or narrowing. The percentage stenosis or narrowing can be calculated from a baseline A1 index of the artery in issue, such that: the % Stenosis or narrowing={1−[A1 (local baseline)/A1 (at stenosis or narrowing)]}×100. Determination of artery stenosis without stiffness is indicative of inflammation or soft plaque formation whereas artery stenosis with stiffness would indicate hard plaque formation.

Thus, while there has been shown and described, fundamental novel features of the disclosure as applied to various specific embodiments thereof, it will be understood that various omissions and substitutions and changes in the form and details of the apparatus illustrated, and in their operation, may be made by those skilled in the art without departing from the spirit of the disclosure. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A system for calculating an arterial compliance index for determining the arterial stiffness of an artery of a subject consisting of:
   a blood pressure monitoring device configured to measure a systolic blood pressure reading and a diastolic blood pressure reading for the artery of the subject;
   a blood flow velocity monitoring device configured to measure a peak-systolic blood flow velocity, wherein the peak-systolic blood flow velocity is a first measure of velocity of blood flowing within the artery of the subject at a peak point of a systolic phase of contraction of the subject's heart muscle, and an end-diastolic blood flow velocity, wherein the end-diastolic blood flow velocity is a second measure of velocity of blood flowing within the artery of the subject at an end point of a diastolic phase of relaxation of the subject's heart muscle; and
   a central processing unit configured to calculate the arterial compliance index as a function of the subject's:
   (a) systolic blood pressure reading as measured by the blood pressure monitoring device,
   (b) diastolic blood pressure reading as measured by the blood pressure monitoring device,
   (c) peak-systolic blood flow velocity determined during the systolic phase of contraction of the subject's heart muscle, and
   (d) end-diastolic blood flow velocity determined during a period of relaxation of the subject's heart muscle.

2. The system of claim 1, wherein the central processing unit is configured to calculate the arterial compliance index as a further function of systolic pressure, pulse pressure and a systolic resistive index, wherein the pulse pressure is defined as the difference between the systolic pressure and diastolic pressure and the systolic resistive index is a quotient determined by a proportion of a first part, wherein the first part is the difference between the peak-systolic velocity and end-diastolic velocity, and a second part, wherein the second part is the peak-systolic velocity.

3. The system of claim 1, wherein the central processing unit is configured to calculate the arterial compliance index as a further function of diastolic pressure, pulse pressure and a diastolic resistive index, wherein the pulse pressure is defined as the difference between the systolic pressure and diastolic pressure and the diastolic resistive index is a quotient determined by a proportion of a first part, wherein the first part is the difference between the peak-systolic velocity and end-diastolic velocity, and a second part, wherein the second part is the end-diastolic velocity.

4. The system of claim 1, wherein the central processing unit is configured to calculate the arterial compliance index as a further function of diastolic pressure, systolic pressure, end-diastolic velocity and peak-systolic velocity, wherein the arterial compliance index is a quotient determined by a proportion of a first part, wherein the first part is the difference between a first product of the peak-systolic velocity and the diastolic pressure and a second product of the end diastolic velocity and the systolic pressure, and a second part, wherein the second part is the difference between the peak-systolic velocity and end-systolic velocity.

5. The system of claim 1, wherein the central processing unit is configured to calculate the arterial compliance index as a further function of:
   (a) a first area index of the artery, wherein the first area index of the artery is a quotient determined by a proportion of a first part, wherein the first part is the difference in peak-systolic velocity and end-diastolic velocity and a second part, wherein the second part is the difference in systolic pressure and diastolic pressure, and
   (b) a second area index of the artery, wherein the second area index of the artery represents the area of the artery that is generating an arterial elastic recoil pressure for continuous flow during the systolic and diastolic phases.

6. The system of claim 1, wherein the central processing unit is configured to calculate the arterial compliance index as a further function of:
   (a) a first area index of the artery, wherein the first area index of the artery is a quotient determined by a proportion of a first part, wherein the first part is the difference in peak-systolic velocity and end-diastolic velocity and a second part, wherein the second part is the difference in systolic pressure and diastolic pressure, and
   (b) the stiffness limit of the artery, wherein the stiffness limit of the artery is defined to be at a point where the first area index of the artery is substantially equal to a second area index of the artery, wherein the second area index of the artery represents the area of the artery that is generating an arterial elastic recoil pressure for continuous flow during the systolic and diastolic phases.

7. The system of claim 1, wherein the central processing unit is configured to calculate the arterial compliance index by selectably employing at least one of the following:
(a) pulse pressure;
(b) systolic vascular resistance pressure;
(c) diastolic vascular resistance pressure;
(d) systolic resistive index;
(e) diastolic resistive index;
(f) vascular resistance index; or
(g) cardiac output index.

8. The system of claim 1, wherein the central processing unit interfaces with the blood pressure monitoring device.

9. The system of claim 1, wherein the central processing unit interfaces with the blood flow velocity monitoring device.

10. The system of claim 1, wherein the central processing unit interfaces with the blood pressure monitoring device and with the blood flow velocity monitoring device.

11. The system of claim 1, wherein the blood pressure monitoring device, the blood flow velocity monitoring device, and the central processing unit, comprise a single unitary device.

12. The system of claim 1, wherein the central processing unit receives blood pressure readings by selectably employing at least one of the following:
(a) key data entry;
(b) electronic data transfer; or
(c) wireless data transfer.

13. The system of claim 1, wherein the central processing unit receives blood velocity readings by selectably employing at least one of the following:
(a) key data entry;
(b) electronic data transfer; or
(c) wireless data transfer.

14. The system of claim 1, wherein the blood pressure monitoring device is a brachial cuff blood pressure device.

15. The system of claim 1, wherein the blood pressure monitoring device is a catheter.

16. The system of claim 1, wherein the blood pressure monitoring device is configured to measure the blood pressure of the subject by measuring the blood pressure at one or more segments of a limb of the subject.

17. The system of claim 1, wherein the blood pressure monitoring device is configured to measure the blood pressure of the subject by measuring the blood pressure at one or more segments of an artery of the subject.

18. The system of claim 1, wherein the blood flow velocity monitoring device is a Doppler ultrasound.

19. The system of claim 1, wherein the blood flow velocity monitoring device is a magnetic resonance imaging device.

20. The system of claim 1, wherein the blood flow velocity monitoring device is configured to measure the blood flow of the subject by measuring the blood flow velocity at one or more segments of at least one artery of the subject.

21. The system of claim 1, wherein the arterial compliance index is determined in real time or near real time.

22. A method for calculating an arterial compliance index for determining the arterial stiffness of an artery of a subject consisting of:
providing a blood pressure monitoring device to measure a systolic blood pressure reading and a diastolic blood pressure reading for the artery of the subject;
determining the systolic blood pressure reading for the subject;
determining the diastolic blood pressure reading for the subject;
configuring a blood flow velocity monitoring device to measure a peak-systolic blood flow velocity, wherein the peak-systolic blood flow velocity is a first measure of velocity of blood flowing within the artery of the subject at a peak point of a systolic phase of contraction of the subject's heart muscle, and an end-diastolic blood flow velocity, wherein the end-diastolic blood flow velocity is a second measure of velocity of blood flowing within the artery of the subject at an end point of a diastolic phase of relaxation of the subject's heart muscle;
determining the peak-systolic blood flow velocity, wherein the peak-systolic blood flow velocity is the velocity of blood flowing within the artery of the subject at a peak point of a systolic phase of contraction of the subject's heart muscle;
determining the end-diastolic blood flow velocity, wherein the end-diastolic blood flow velocity is the velocity of blood flowing within the artery of the subject at an end point of a diastolic phase of relaxation of the subject's heart muscle; and
configuring a central processing unit to calculate the arterial compliance index as a function of the subject's:
(a) systolic blood pressure reading as measured by the blood pressure monitoring device,
(b) diastolic blood pressure reading as measured by the blood pressure monitoring device,
(c) peak-systolic blood flow velocity determined during the systolic phase of contraction of the subject's heart muscle, and
(d) end-diastolic blood flow velocity determined during a period of relaxation of the subject's heart muscle.

23. The method of claim 22, wherein the central processing unit is further configured to calculate the arterial compliance index as a function of systolic pressure, pulse pressure and a systolic resistive index, wherein the pulse pressure is the difference between the systolic pressure and diastolic pressure and the systolic resistive index is a quotient determined by a proportion of a first part, wherein the first part is the difference between the peak-systolic velocity and end-diastolic velocity, and a second part, wherein the second part is the peak-systolic velocity.

24. The method of claim 22, wherein the central processing unit is further configured to calculate the arterial compliance index as a function of diastolic pressure, pulse pressure and a diastolic resistive index, wherein the pulse pressure is the difference between the systolic pressure and diastolic pressure and the diastolic resistive index is a quotient determined by a proportion of a first part, wherein the first part is the difference between the peak-systolic velocity and end-diastolic velocity, and a second part, wherein the second part is the end-diastolic velocity.

25. The method of claim 22, wherein the central processing unit is configured to calculate the arterial compliance index as a further function of diastolic pressure, systolic pressure, end-diastolic velocity and peak-systolic velocity, wherein the arterial compliance index is a quotient determined by a proportion of a first part, wherein the first part is the difference between a first product of the peak-systolic velocity and the diastolic pressure and a second product of the end-diastolic velocity and the systolic pressure, and a second part, wherein the second part is the difference between the peak-systolic velocity and end-systolic velocity.

26. The method of claim 22, wherein the central processing unit is configured to calculate the arterial compliance index as a further function of:
(a) a first area index of the artery, wherein the first area index of the artery is a quotient determined by a proportion of a first part, wherein the first part is the difference in peak-systolic velocity and end-diastolic velocity and a second part, wherein the second part is the difference in systolic pressure and diastolic pressure, and (b) a second area index of the artery, wherein the second area of the artery represents the area of the artery that is generating an arterial elastic recoil pressure for continuous flow during the systolic and diastolic phases.

27. The method of claim 22, wherein the central processing unit is configured to calculate the arterial compliance index as a function of:

(a) a first area index of the artery, wherein the first area index of the artery is a quotient determined by a proportion of a first part, wherein the first part is the difference in peak-systolic velocity and end-diastolic velocity and a second part, wherein the second part is the difference in systolic pressure and diastolic pressure, and (b) the stiffness limit of the artery, wherein the stiffness limit of the artery is defined to be at a point where the first area index of the artery is substantially equal to a second area index of the artery, wherein the second area of the artery represents the area of the artery that is generating an arterial elastic recoil pressure for continuous flow during the systolic and diastolic phases.

28. The method of claim 22, wherein the central processing unit is further configured to calculate the arterial compliance index by selectably employing at least one of the following:

(a) pulse pressure;
(b) systolic vascular resistance pressure;
(c) diastolic vascular resistance pressure;
(d) systolic resistive index;
(e) diastolic resistive index;
(f) vascular resistance index; or
(g) cardiac output index.

29. The method of claim 22, further comprising comparing the arterial compliance index of the artery of the subject with a second arterial compliance index derived from a mean reading of a segment of a population.

30. The method of claim 22, further comprising comparing the arterial compliance index of the artery of the subject with a second arterial compliance index derived from one or more segments of the artery.

\* \* \* \* \*